United States Patent [19]
Scott et al.

[11] Patent Number: 5,481,060
[45] Date of Patent: Jan. 2, 1996

[54] PROCESS FOR THE REMOVAL OF HEAVY HYDROCARBONACEOUS CO-PRODUCTS FROM A VAPOR EFFLUENT FROM A NORMALLY GASEOUS HYDROCARBON DEHYDROGENATION REACTION ZONE

[75] Inventors: Norman H. Scott; Joseph E. Zimmermann, both of Arlington Heights; Bryan K. Glover, Algonquin, all of Ill.

[73] Assignee: UOP, Des Plaines, Ill.

[21] Appl. No.: 425,520

[22] Filed: Apr. 20, 1995

[51] Int. Cl.⁶ ..................... C07C 7/00
[52] U.S. Cl. ..................... 585/867
[58] Field of Search ..................... 585/867

[56] References Cited

U.S. PATENT DOCUMENTS

| | | | |
|---|---|---|---|
| 4,430,517 | 2/1984 | Imai et al. | 585/660 |
| 4,822,948 | 4/1989 | Larue et al. | 585/867 |

Primary Examiner—Sharon Gibson
Assistant Examiner—Nhat D. Phan
Attorney, Agent, or Firm—Thomas K. McBride; John G. Tolomei; John G. Cutts, Jr.

[57] ABSTRACT

A process for the removal of trace quantities of polynuclear aromatic compounds from the vapor effluent of a hydrocarbon dehydrogenation zone containing normally gaseous olefinic hydrocarbons, trace mononuclear aromatic compounds and trace polynuclear aromatic compounds by contacting the vapor effluent of a hydrocarbon dehydrogenation zone with a lean liquid absorption stream comprising at least one mononuclear aromatic compound to absorb at least a portion of the trace mononuclear aromatic compounds and the trace polynuclear aromatic compounds to produce a rich liquid absorption stream and a gaseous olefin-containing hydrocarbon stream having a reduced concentration of mononuclear aromatic compounds and polynuclear aromatic compounds. The rich liquid absorption stream is separated to produce a stream rich in mononuclear aromatic compounds and a stream comprising polynuclear aromatic compounds. At least a portion of the stream rich in mononuclear aromatic compounds is recycled to provide at least a portion of the lean liquid absorption stream.

8 Claims, 1 Drawing Sheet

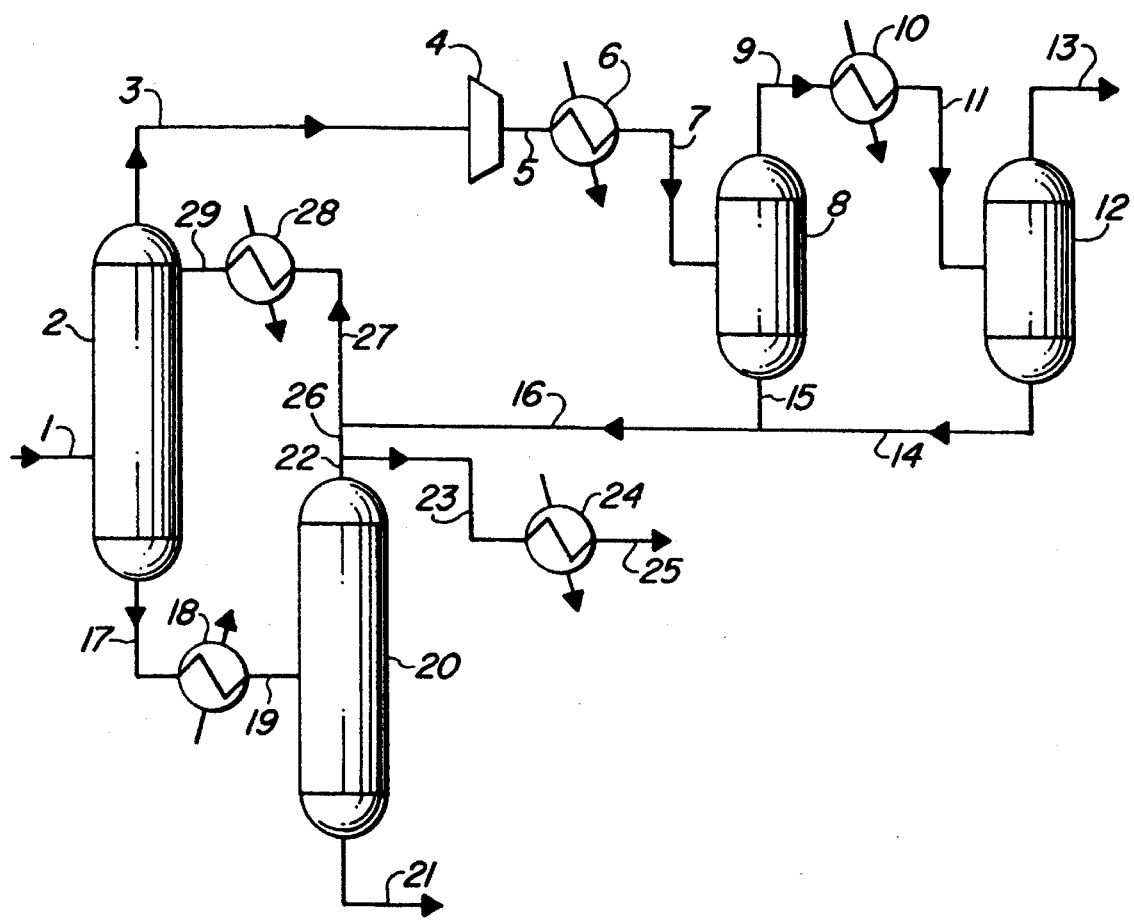

PROCESS FOR THE REMOVAL OF HEAVY HYDROCARBONACEOUS CO-PRODUCTS FROM A VAPOR EFFLUENT FROM A NORMALLY GASEOUS HYDROCARBON DEHYDROGENATION REACTION ZONE

FIELD OF THE INVENTION

The field of art to which this invention pertains is the removal and recovery of heavy hydrocarbonaceous co-products including mononuclear and polynuclear aromatic compounds from the vapor effluent from a normally gaseous hydrocarbon dehydrogenation reaction zone.

BACKGROUND OF THE INVENTION

The dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers and other products which are well known to those skilled in the art. One example of this process is the dehydrogenation of isobutane to produce isobutylene which can be polymerized to provide tackifying agents for adhesives, viscosity-index additives for motor oils and impact-resistant and anti-oxidant additives for plastics. Another example of the growing demand for isobutylene is the production of oxygen-containing gasoline blending components which are being mandated by the government in order to reduce air pollution from automotive emissions.

Those skilled in the art of hydrocarbon conversion processing are well versed in the production of olefins by means of catalytic dehydrogenation of paraffinic hydrocarbons. In addition, many patents have issued which teach and discuss the dehydrogenation of hydrocarbons in general. For example, U.S. Pat. No. 4,430,517 issued to Imai et al discusses a dehydrogenation process and catalyst for use therein.

Despite the fact that the dehydrogenation of paraffinic hydrocarbons is well known, the more widespread usage of this processing technology and greater severity operation of existing commercial facilities has highlighted the problem which occurs in the product recovery section of hydrocarbon dehydrogenation processes. This problem is the result of the co-production of trace quantities of mononuclear aromatic and polynuclear aromatic compounds. The mononuclear aromatic compounds are considered to be an undesired impurity in the desired olefinic hydrocarbon product stream and must be removed. The polynuclear aromatic compounds are not only an undesired impurity, but also present a severe operational problem because when they condense and plate out on the cooler surfaces of the plant there are detrimental results. The deposits of polynuclear aromatic compounds are difficult to remove, they reduce the efficiency of heat exchangers and they may eventually lead to plugging.

Therefore, those skilled in the art of hydrocarbon processing have sought methods to overcome the problem posed by the production of polynuclear aromatic compounds in dehydrogenation production facilities. The process of the present invention provides a facile and economical solution to the problem of the co-production of mononuclear and polynuclear aromatic compounds in a dehydrogenation plant.

BRIEF SUMMARY OF THE INVENTION

The present invention relates to a process for the removal of trace quantities of polynuclear aromatic compounds from the vapor effluent of a hydrocarbon dehydrogenation zone containing normally gaseous olefinic hydrocarbons and trace quantities of mononuclear and polynuclear aromatic compounds.

One embodiment of the present invention may be characterized as a process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises: (a) contacting the vapor effluent of a hydrocarbon dehydrogenation zone with a lean liquid absorption stream comprising at least one mononuclear aromatic compound to absorb at least a portion of the trace mononuclear aromatic compounds and the trace polynuclear aromatic compounds to produce a rich liquid absorption stream and a gaseous olefinic hydrocarbon stream having a reduced concentration of mononuclear aromatic compounds and polynuclear aromatic compounds; (b) recovering the gaseous olefin-containing hydrocarbon stream having a reduced concentration of mononuclear aromatic compounds and polynuclear aromatic compounds; (c) separating the rich liquid absorption stream from step (a) to produce a stream rich in mononuclear aromatic compounds and a stream comprising polynuclear aromatic compounds; (d) recycling at least a portion of the stream rich in mononuclear aromatic compounds to step (a) to provide at least a portion of the lean liquid absorption stream; and (e) recovering the stream comprising polynuclear aromatic compounds.

Other embodiments of the present invention encompass further details such as preferred absorption solutions and preferred operating conditions.

The process of the present invention provides the advantages of using an indigenous, undesirable co-product, i.e., mononuclear aromatic compounds, to serve as a liquid absorption stream for the purification of normally gaseous olefinic hydrocarbons by the separation of trace quantities of polynuclear aromatic compounds from the olefinic hydrocarbons.

BRIEF DESCRIPTION OF THE DRAWING

The drawing is a simplified process flow diagram of a preferred embodiment of the present invention. The above-described drawing is intended to be schematically illustrative of the present invention and is not to be a limitation thereof.

DETAILED DESCRIPTION OF THE INVENTION

The present invention is a process for the removal of trace quantities of polynuclear aromatic compounds from the vapor effluent of a hydrocarbon dehydrogenation zone. The dehydrogenation of paraffinic hydrocarbons is well known to those skilled in the art of hydrocarbon processing.

In the dehydrogenation process, fresh hydrocarbon feed is combined with recycle hydrogen and unconverted hydrocarbons. This forms a reactant stream which is passed through a bed of suitable dehydrogenation catalyst maintained at the proper dehydrogenation conditions such as temperature, pressure and space velocity, and the effluent from the catalytic reaction zone is processed further to yield a stream of olefinic hydrocarbons. In accordance with the present invention, the effluent from the catalytic reaction zone contains unconverted saturated hydrocarbons, olefin hydrocarbons, mononuclear aromatic compounds in an amount from about 100 to about 5,000 wppm and polynuclear aromatic compounds in an amount from about 50 to about 500 wppm.

In accordance with the present invention, the dehydrogenation reaction zone effluent is preferably cooled to a temperature in the range from about 50° F. (10° C.) to about 150° F. (65° C.) and contacted in a contacting zone with a lean liquid absorption stream containing at least one mononuclear aromatic compound in order to separate and recover the trace quantities of polynuclear aromatic compounds which are contained in the dehydrogenation reaction zone effluent. In a preferred embodiment of the present invention, at least a portion of the mononuclear aromatic compound or compounds in the lean liquid absorption stream is recovered from the dehydrogenation reaction zone effluent. Preferred mononuclear aromatic compounds are selected from the group consisting of benzene, toluene and xylene.

The resulting scrubbed dehydrogenation reaction zone effluent may then be compressed, cooled, subjected to cryogenic refrigeration, treated for chloride removal, treated for water removal or fractionated, for example.

In another preferred embodiment, after the effluent from the hydrocarbon dehydrogenation zone has been contacted with the lean liquid absorption liquid, the resulting gaseous olefinic hydrocarbon stream is compressed to a pressure in the range from about 30 psig (207 kPa gauge) to about 200 psig (1379 kPa gauge), and cooled to a temperature in the range from about 100° F. (38° C.) to about 150° F. (65° C.), and introduced into a vapor-liquid separation zone. A liquid stream is removed from the vapor-liquid separation zone and is introduced into the contacting zone. A vapor stream containing olefinic hydrocarbons is removed from the vapor-liquid separation zone and further chilled to a temperature in the range of about 0° F. (−18° C.) to about 100° F. ( 38° C.) and introduced into a chilled vapor-liquid separation zone. A liquid stream is removed from the chilled vapor-liquid separation zone and is also introduced into the contacting zone. The vapor stream leaving the chilled vapor-liquid separation zone is essentially free of polynuclear aromatic compounds and has a greatly reduced level of mononuclear aromatic compounds. Preferably, the vapor stream contains less than about 10 wppm mononuclear aromatic compounds and less than about 1 wppm polynuclear aromatic compounds.

DETAILED DESCRIPTION OF THE DRAWING

With reference now to the drawing, a vapor effluent from a hydrocarbon dehydrogenation zone containing normally gaseous olefinic hydrocarbons, trace mononuclear aromatic compounds and trace polynuclear aromatic compounds is introduced into the process via conduit 1 and enters absorption zone 2. The vapor effluent is contacted in absorption zone 2 with a hereinafter-described lean absorption solution in order to remove essentially all of the trace mononuclear aromatic compounds and the trace polynuclear aromatic compounds. A resulting vapor stream is removed from absorption zone 2 via conduit 3 and introduced into compressor 4. The resulting compressed gas is removed from compressor 4 via conduit 5 and is cooled in heat exchanger 6. A resulting two-phase stream is removed from heat exchanger 6 via conduit 7 and is introduced into vapor-liquid separator 8. A resulting vapor stream is removed from vapor-liquid separator 8 via conduit 9 and is cooled in heat exchanger 10. A resulting cooled two-phase stream is removed from heat exchanger 10 via conduit 11 and introduced into chilled vapor-liquid separator 12. A vapor stream is removed from chilled vapor-liquid separator 12 via conduit 13 and recovered. A liquid stream is removed from chilled vapor-liquid separator 12 via conduit 14 and a liquid stream is removed from vapor-liquid separator 8 via conduit 15 and these liquid streams are transported via conduit 16. A rich liquid absorption stream is removed from absorption zone 2 via conduit 17, heated in heat exchanger 18 and introduced into stripper 20 via conduit 19. A stream containing polynuclear aromatic compounds is removed from stripper 20 via conduit 21 and recovered. A vapor stream is recovered from stripper 20 via conduit 22 and a portion of this vapor is transported via conduit 23, cooled in heat exchanger 24 and removed from the process via conduit 25 and recovered. Another portion of the vapor removed from stripper 20 is transported via conduit 26 and is admixed with the joined liquid streams which are carried via conduit 16 and the resulting admixture is carried via conduit 27 and introduced into heat exchanger 28. The resulting liquid stream is removed from heat exchanger 28 via conduit 29 and is introduced into absorption zone 2 to serve as the hereinabove-described lean absorption solution.

The process of the present invention is further demonstrated by the following illustrative embodiment. This illustrative embodiment is, however, not presented to unduly limit the process of this invention, but to further illustrate the advantages of the hereinabovedescribed embodiment. The following data were not obtained by the actual performance of the present invention, but are considered prospective and reasonably illustrative of the expected performance of the invention.

ILLUSTRATIVE EMBODIMENT

An effluent from a propane-isobutane dehydrogenation zone having the characteristics and flow rates presented in Table 1 is introduced into a countercurrent absorption zone and is contacted with a lean liquid absorber solution having the characteristics and flow rates also presented in Table 1. A resulting gaseous stream is removed from the countercurrent absorption zone having the characteristics and flow rates presented in Table 1. This gaseous stream is compressed, cooled and subjected to a first vapor-liquid separation zone to produce a gaseous stream identified as Gas A having the characteristics and flow rates presented in Table 2. A liquid stream identified as Liquid A is recovered from the first vapor-liquid separation zone having the characteristics and flow rates presented in Table 2. Gas A is further chilled and subjected to a second vapor-liquid separation zone to produce a gaseous stream, Gas B, and a liquid stream, Liquid B, both having the characteristics and flow rates presented in Table 2.

Liquid A and Liquid B are combined and provide a portion of the lean liquid absorber solution. A rich absorber solution containing mononuclear and polynuclear aromatic compounds which were removed from the feed gas is removed from the absorption zone and introduced into a stripper column. A portion of the overhead vapor from the stripper column is condensed and provides another portion of the lean liquid absorber solution. Another portion of the vapor from the stripper column is condensed and recovered as a net liquid stream containing essentially all of the mononuclear aromatic compounds contained in the feed gas.

A net stripper bottoms is removed and recovered which contains essentially all of the polynuclear aromatic compounds.

The foregoing description and illustrative embodiment clearly illustrate the advantages encompassed by the method of the present invention and the befits to be afforded with the use thereof.

TABLE 1

STREAM ANALYSIS

| Component, Pound-Mol/Hr | Feed | Lean Liquid Absorber Solution | Absorber Off-Gas |
|---|---|---|---|
| Hydrogen | 5823 | — | 5825 |
| Methane, | 630 | — | 632 |
| Ethylene / Ethane | 119 | — | 121 |
| Propylene | 627 | 2 | 666 |
| Propane | 1205 | 4 | 1293 |
| Isobutane | 1300 | 11 | 1529 |
| Isobutylene | 1176 | 13 | 1418 |
| Mononuclear aromatic compounds | 7 | 356 | 210 |
| Polynuclear aromatic compounds | 0.1 | — | 0.1 |

TABLE 2

STREAM ANALYSIS

| Component, Pound-Mol/Hr | Gas A | Liquid A | Gas B | Liquid B |
|---|---|---|---|---|
| Hydrogen, pound-mol/hr | 5825 | — | 5823 | 2 |
| Methane, | 632 | — | 630 | 2 |
| Ethylene / Ethane | 121 | — | 119 | 2 |
| Propylene | 659 | 7 | 627 | 32 |
| Propane | 1278 | 15 | 1205 | 73 |
| Isobutane | 1489 | 40 | 1298 | 191 |
| Isobutylene | 1375 | 43 | 1175 | 200 |
| Mononuclear aromatic compounds | 41 | 169 | 1 | 40 |
| Polynuclear aromatic compounds | — | 0.1 | — | — |

What is claimed is:

1. A process for the removal of trace quantities of polynuclear aromatic compounds from the vapor effluent of a hydrocarbon dehydrogenation zone comprising normally gaseous olefinic hydrocarbons, trace mononuclear aromatic compounds and trace polynuclear aromatic compounds which process comprises:

(a) contacting said vapor effluent of a hydrocarbon dehydrogenation zone with a lean liquid absorption stream comprising at least one mononuclear aromatic compound to absorb at least a portion of said trace mononuclear aromatic compounds and said trace polynuclear aromatic compounds to produce a rich liquid absorption stream and a gaseous olefinic hydrocarbon stream having a reduced concentration of mononuclear aromatic compounds and polynuclear aromatic compounds;

(b) recovering said gaseous olefin-containing hydrocarbon stream having a reduced concentration of mononuclear aromatic compounds and polynuclear aromatic compounds;

(c) separating said rich liquid absorption stream from step (a) to produce a stream rich in mononuclear aromatic compounds and a stream comprising polynuclear aromatic compounds;

(d) recycling at least a portion of said stream rich in mononuclear aromatic compounds to step (a) to provide at least a portion of said lean liquid absorption stream; and (e) recovering said stream comprising polynuclear aromatic compounds.

2. The process of claim 1 wherein said normally gaseous olefinic hydrocarbons are selected from the group consisting of ethylene, propylene and butylene.

3. The process of claim 1 wherein said mononuclear aromatic compounds is selected from the group consisting of benzene, toluene and xylene.

4. The process of claim 1 wherein the trace quantities of polynuclear aromatic compounds are present in the vapor effluent of a dehydrogenation zone in an amount from about 50 to about 500 wppm.

5. The process of claim 1 wherein the trace quantities of mononuclear aromatic compounds are present in the vapor effluent of a dehydrogenation zone in an amount from about 100 to about 5000 wppm.

6. The process of claim 1 wherein said contacting in step (a) is conducted in a countercurrent vapor-liquid extraction zone.

7. The process of claim 1 wherein said gaseous olefin-containing hydrocarbon stream having a reduced concentration of mononuclear aromatic compounds and polynuclear aromatic compounds contains less than about 10 wppm mononuclear aromatic compounds and less than about 1 wppm polynuclear aromatic compounds.

8. The process of claim 1 wherein a net stream of mononuclear aromatic compounds is recovered.

* * * * *